United States Patent [19]

Godbille et al.

[11] 4,411,658
[45] Oct. 25, 1983

[54] DEVICE FOR ADMINISTERING

[75] Inventors: Etienne Godbille, Villemomble; Pierre Escuret, Paris; Jean-Pierre Scheid, Vaujours, all of France

[73] Assignee: Roussel Uclaf, Romainville, France

[21] Appl. No.: 234,841

[22] Filed: Feb. 17, 1981

[30] Foreign Application Priority Data

Feb. 18, 1980 [FR] France ................................. 8003478

[51] Int. Cl.³ .............................................. A61M 7/00
[52] U.S. Cl. ...................................... 604/285; 604/892
[58] Field of Search ............................... 128/127–131, 128/260–261, 270; 604/285–288, 892

[56] References Cited

U.S. PATENT DOCUMENTS

| | | | |
|---|---|---|---|
| 3,777,015 | 12/1973 | Zaffaroni | 128/130 |
| 3,820,535 | 6/1974 | Marco | 128/130 |
| 3,916,898 | 11/1975 | Robinson | 128/270 |
| 3,920,805 | 11/1975 | Roseman | 128/130 |
| 3,981,305 | 9/1976 | Ring | 128/130 |
| 3,991,760 | 11/1976 | Drobish et al. | 128/127 |
| 4,066,075 | 1/1978 | Hughes | 128/127 |
| 4,286,587 | 9/1981 | Wong | 128/127 |
| 4,292,965 | 10/1981 | Nash et al. | 128/127 |

FOREIGN PATENT DOCUMENTS

| | | | |
|---|---|---|---|
| 470839 | 6/1914 | France . | |
| 1058194 | 11/1953 | France | 128/127 |

OTHER PUBLICATIONS

*The Merck Index*, 9th Ed., Merck & Co., Inc. Rahway, N.J., 1976, pp. 3636–3637.

*Primary Examiner*—C. Fred Rosenbaum
*Attorney, Agent, or Firm*—Bacon & Thomas

[57] ABSTRACT

A device for the vaginal administration of medicinal substances comprising a flat, supple, elastically deformable plastic material having a constant thickness and shaped in the form of a star having at least three identical arms having constant width and rounded extremities containing at least one biologically active substance is disclosed.

6 Claims, 2 Drawing Figures

DEVICE FOR ADMINISTERING

The subject of the present invention is a device for administering medicinal substances. More particularly, the device is for the administration of medicinal substances through the mucous membranes of the walls of the vagina.

There are numerous known devices and methods for preventive and curative treatment, for diagnosis, or for modification of the physiological functions in warm-blooded living beings using this route of administration. A great variety of such devices and methods are particularly used in the animal domain. One current example of the use of these devices is the synchronization of oestrus in cattle, sheep and horses. This use requires a certain concentration of gestogenic substances during a period of about two weeks, at the end of which it is necessary to quickly eliminate the active substances in order that a new cycle can begin.

Among the methods and devices used for this purpose include those which are applied by the genito-urinary route. The devices used in these cases are, for example, sponges, tampons, tubes filled with active substances, ovules, etc. The active substances, for which these devices are the carriers, are put into contact with the vaginal mucous membranes and absorbed by this route.

Certain devices, such as for example the ovules, are made in such a manner as to dissolve as the active substances they contain are absorbed. Other devices, such as for example, tampons or sponges, are made of a biologically inactive insoluble substance and are carriers of active substances. These substances can be applied to, coated on, or incorporated in the devices.

When such a device is a vaginal implant having the form of a tube it can be made also of a biologically inactive insoluble material and the substance can be placed on a support inside the tube, or even incorporated in the mass of the latter.

The biologically inactive materials that can be used in such devices are for example those with a base of silicon elastomers, in which the active material or materials are introduced when they are polymerized.

Generally, these devices achieve their object in a more or less satisfactory manner. Nevertheless, the use of these devices can present some inconveniences.

Thus, for example, some of them cannot easily be withdrawn from the vaginal cavity at the desired time. Often it happens that they can only be withdrawn partially, while leaving in the vaginal cavity residues which are still carriers of the active substance. For this reason the ability to stop the administration of the active substances at a precise moment cannot be accomplished.

Some of these devices have to have small dimensions in order to more easily be introduced into or extracted from the vaginal cavity. Because of this the surface of contact between such a device and the mucous membranes of the vaginal wall is reduced, and therefore the optimum absorption conditions of the active substances which are carried by the device is reduced.

Moreover, some of these devices, as for example, the tubes and tampons, are not well tolerated by the organism. They can also cause inflammations of the vaginal wall, in particular the bottom of the vaginal cavity and of the neck of the uterus. It can also happen that they cause internal contractions, which often results in the rejection of these devices.

These deficiencies are overcome by the device for the administration of medicinal materials which is the subject of the present invention. This device comprises flexible parts with the active materials incorporated in its mass. It is made of a biologically inactive flexible material and it is characterized in that:

It consists of a flat piece of constant thickness in the shape of a star with at least three identical arms having a constant width and rounded ends;

It is supple and easily and elastically deformable.

The device of the invention can further be characterized in that:

The ends and the edges of the arms of the star are rounded; It is provided with a means for giving it a spherical-like shape and which comprises a flexible cord for maintaining it, fixed to the centre of the star shaped device;

It is made of a plastic material which can be polymerized at a temperature near to room temperature; The star shaped device contains from 0.1 to 30% by weight of active substances;

It can be used with active substances having a therapeutic or prophylactic effect or an effect on the physiological functions of the animal. It may also be used for diagnosis. Active substances which may be used include oestrogens, androgens, gestogens, disinfectants and anti-parasitics, and preferably 3-oxo 17α-allyl 17β-hydroxy 4,9(10),11-estratriene.

Placement of the device which is the subject of the invention in the vaginal cavity is done by giving it a spherical-like form by bending the arms of the star, in which shape it is made, in the direction opposite to the direction of its introduction into the vaginal cavity.

The device of the invention may be easily removed by pulling on the manipulation cord, which causes the device to assume a spherical-like form by bending the arms of the star, due to traction from the vaginal wall, in the direction opposite to the direction of removal.

An alternative embodiment of variant of the device of the invention is characterized in that it includes means to provide it with the spherical-like form without external traction. This means comprises flexible connections joining the ends of each of the arms of the star, to a central point on the axis of the star, in such a way as to bend the arms and impart an initial spherical-like form to the device. The central point may be further attached to a manipulation cord, pulling on which enables the spherical deformation to be increased if desired, and at the same time, facilitates the introduction into and the removal from the vaginal cavity of the device.

Because of its structural arrangement and elasticity, the arms of the star, in which shape the flat piece is made, can easily be bent so as to ensure the easy placing in and removal from the vaginal cavity. Preferably, the active substance or substances are incorporated in the plastic material of which the flat piece is made. The plastic material of which it is made is a polymeric elastomer with a silicon base, such as polysiloxane.

The star, in which shape the flat piece is made, can have a diameter of from 20 to 150 mm and a thickness from 1 to 15 mm according to the animal species for which the device is to be used. For example, for cows the diameter of the star may be 90 mm with a thickness of 3 mm, while for mares the diameter may be 120 mm with a thickness of 7 mm. These are examples and the dimensions will vary with the particular groups of animals. However, the optimum dimensions can be determined without undue experimentation. The size of the star cannot be too large or it will cause contractions and discomfort. If it is too small it will not remain properly and securely in place. For animals other than cows and mares, the dimensions of the star will depend upon the size of the vaginal cavity.

The arms of the star have a width of from 4 to 60 mm, depending on the diameter of the star. The length of the arms of the star represent from 75 to 90% of the overall diameter of the star, i.e., the diameter to the rounded extremities or ends of the star. For example, a star having an overall diameter of from 25 to 35 mm would have arms from 20 to 30 mm in length. The exact ratio or percentage of arm length to star diameter is determined to provide optimal folding of the arms of the star to allow the device to take a spherical-like form. If the arms are too short, the desired spherical-like shape is not obtained. Moreover, longer arms are preferred as they ensure good anchorage of the device when place in the vaginal cavity.

The number of arms on the star may vary but there should be at least three arms. There may be an odd or even number of arms. Preferably, there are five arms since a device with five arms has been found to be most efficiently retained in place in the vaginal cavity.

The manipulation cord attached to the center of the star, as well as the flexible connections attached to the extremities of the arms in the case of the variant of the device of the invention, can be introduced and anchored in the mass of the body of the star at the time of its fabrication, or fixed by conventional means, such as by knots, after fabrication. Also, the two methods can be combined. The manipulation cord is made of known materials. The length of the manipulating cord is chosen according to the depth of the vaginal cavity of the animal species. Thus, for example, for cattle it will be from 40 to 70 cm; for horses from 50 to 90 cm; for sheep from 25 to 55 cm.

The polymeric material of which the device is made may be any material which may be polymerized at a temperature which does not damage the active material incorporated therein. This is preferably at ambient or room temperature which will not degrade the preferred active material 3-oxo 17α-allyl 17β-hydroxy 4,9(1),11-estratriene. In addition, the polymeric material must be sufficiently elastic to enable the device to assume a spherical-like shape under tension, but strong enough not to rupture on removal from the vagina.

The polymeric material must be soft so that it does not irritate the animal's mucous membranes and capable of releasing the active material contained therein when it is placed in the animal's vagina. It has been found the silicone polymers meet these requirements, in particular, "Rhodorsil RTC 1502" and "Rhodorsil RTV III" manufactured by Rhone-Poulenc. The mechanical properties of polymers of these materials are respectively:

|  | RTV 1502 | RTV III |
|---|---|---|
| Tear Strength | 20 kg/cm | 2.8 kg/cm |
| Elongation at Break | 600% | 200% |
| Shore Hardness | 30 | 47 |

An example of a method for making the star shaped device of the present invention is as follows:

A flowable or pourable composition is prepared at room temperature by mixing the following ingredients:
20.632 grams of "Rhodorsil RTV 1502"
2.063 grams of catalyst 1502 B
2.063 grams of silicone oil
0.040 grams lampblack
0.200 grams active material The mixture, at room temperature, is poured into a star mold, degassed under vacuum, allowed to polymerize for 72 hours and the star device is then removed from the mold. The silicone oil is added to facilitate moulding of the composition and removal of the formed star from the mold. Lampblack is added as a coloring pigment to protect the active material from visible and ultraviolet radiation. The catalyst 1502-B which is provided with the "Rhodorsil RTC-1502", catalyzes the polymerization reaction.

The device according to the invention offers the following advantages:

It presents a very large surface of contact with the mucous membrane of the vaginal wall, and for this reason the absorption is improved and better controlled;

Because of its flexibility, the risk of causing disturbing contacts and inflammations of the vaginal wall and of the neck of the uterus is diminished. This is also true for the internal contractions and the rejection of the device, which are suppressed;

Putting the present device in place is easy;

Its removal from the vaginal cavity is eased and does not offer risks of tearing during this operation; pieces cannot remain in the organism, for which reason one can be sure that after extraction of the device no traces of the active substances remain.

The attached drawings shown, by way of example, schematic forms of the device which is the subject of the invention.

In these drawings the dimensions are often exaggerated so that they are easier to read.

Figure 1:
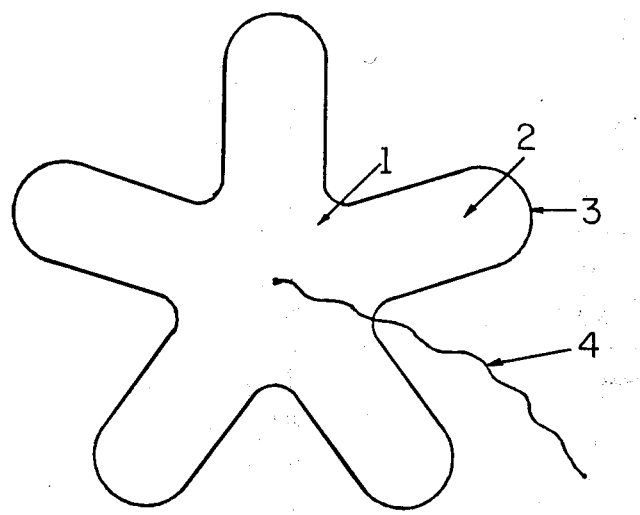
FIG. 1 is a schematic plane view of the device of the invention.
Figure 2:
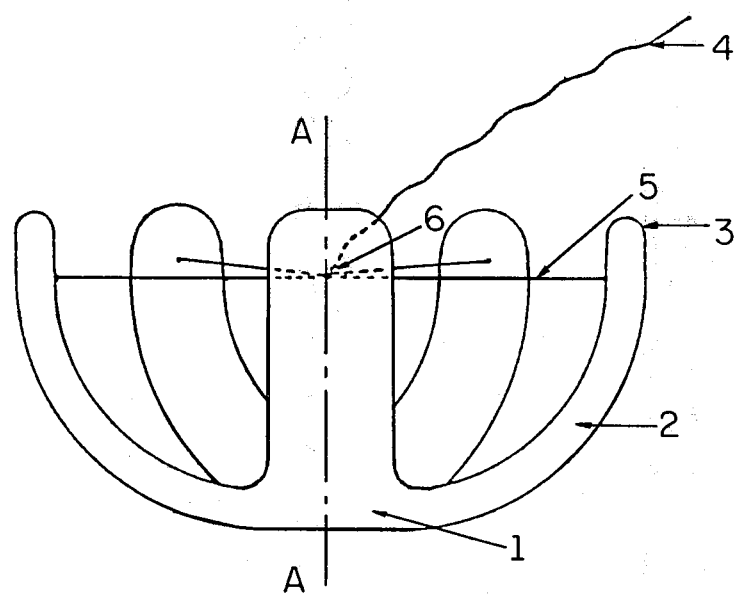
FIG. 2 is a schematic elevated view of the variant of the device of the invention.

The reference numerals in the drawings are as follows:

(1)—represents the star in which shape the flat piece is made.

(2)—An arm of the said star (1)

(3)—The rounded extremity of the said arm (2)

(4)—The manipulating cord.

(5)—The flexible connections from the extremities (3) of each of the arms (2) of the star (1) to a central point (6) on the axis A—A of the said star (1).

One proceeds to put the device of the invention in place by bending as necessary the arms of the star, and by introducing the device into the vaginal cavity. This process can be facilitated if, for example, the introduction is made with the help of a tube. In this case the star is bent, placed in the tube, and when the tube is introduced into the vaginal cavity, ejected from the tube by means of a piston, for example. With animal species of larger dimensions the insertion can be done by hand.

Once the device of the invention is in place, it takes up the shape and the dimension of the vaginal cavity because of its suppleness and for the same reason enters into contact with the mucuous membrane of the vaginal wall. The active substance or substances incorporated in the molecular network of the polymer enter into contact with the moist ambient surroundings, first dissolving or dispersing, and then being absorbed by the mucous membrane of the vaginal wall.

When extracting the device of the invention from the vaginal cavity, it suffices to pull on the manipulating cord. This traction, because of the suppleness of the device, enables it to deform in such a way that the arms of the star become bent in the direction opposed to the extraction. For this reason, when being extracted, the star easily takes up the shapes and the dimensions of the vaginal cavity, and the operation can be effected without any difficulty.

When the device of the invention is made in the form of its variant, in which the arms of the star are bent and tied to a central point by means of flexible connections, putting it in place is done as previously described by means of, for example, a tube. In larger animal species, it can be put in place by hand.

When this variant of the device is being extracted from the vaginal cavity, pulling on the manipulating cord causes, according to the resistance which the vaginal cavity opposes by reason of its shape and dimensions, an easy and sufficient deformation of the said star so that it can be extracted easily.

What is claimed is:

1. A device for the vaginal administration of medicinal substances comprising a flat, supple, elastically deformable biologically inactive material having a constant thickness and shaped in the form of a star having at least three identical arms having constant width and rounded extremities containing at least one biologically active substance incorporated in its mass and having means for imparting a spherical-like form which comprises a flexible manipulating cord fixed to the centre of the star shaped flat piece.

2. A device for the vaginal administration of medicinal substances comprising a flat, supple, elastically deformable biologically inactive plastic material having a constant thickness and shaped in the form of a star having at least three identical arms having constant width and rounded extremities containing at least one biologically active substance incorporated in its mass and which includes a spherical forming means comprising flexible connections from the extremity of each of the arms of the star to a central point of the axis of the star, thereby causing the arms to bend and thus imparting to the device a initial spherical-like form; said central point being further attached to a manipulating cord, the pulling of which enables the spherical deformation of the device to be increased and facilitate the extraction of the device from the vaginal cavity.

3. The device according to the claims 1 or 2 wherein the plastic material is formed by polymerization at a temperature near to ambient temperature.

4. The device according to claims 1 or 2 wherein the active substance is present in an amount of from 0.1 to 30% by weight.

5. The device according to claims 1 or 2 wherein the active substance has a therapeutic or prophylactic effect, or acts on the physiological functions, or is effective for diagnosis.

6. The device according to claims 1 or 2 wherein the active substance is 3-oxo 17α-allyl 17β-hydroxy 4,9(10), 11-estratriene.

* * * * *